United States Patent
Taniguchi et al.

(10) Patent No.: US 9,474,656 B2
(45) Date of Patent: Oct. 25, 2016

(54) TAMPON APPLICATOR

(75) Inventors: Kenta Taniguchi, Kagawa (JP);
Yukihiro Ito, Kagawa (JP); Kouichi Yamaki, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 83 days.

(21) Appl. No.: 14/235,726

(22) PCT Filed: Jul. 26, 2012

(86) PCT No.: PCT/JP2012/068994
§ 371 (c)(1),
(2), (4) Date: Jan. 28, 2014

(87) PCT Pub. No.: WO2013/018655
PCT Pub. Date: Feb. 7, 2013

(65) Prior Publication Data
US 2014/0155809 A1 Jun. 5, 2014

(30) Foreign Application Priority Data
Jul. 29, 2011 (JP) .................................. 2011-167807

(51) Int. Cl.
*A61F 13/32* (2006.01)
*A61F 13/26* (2006.01)

(52) U.S. Cl.
CPC .................................. *A61F 13/266* (2013.01)

(58) Field of Classification Search
CPC .............................. A61F 13/26; A61F 13/266
USPC .............................................. 604/14, 15, 18
See application file for complete search history.

(56) References Cited

U.S. PATENT DOCUMENTS

| | | | | |
|---|---|---|---|---|
| 4,048,998 A | * | 9/1977 | Nigro | A61F 13/263 604/14 |
| 4,125,113 A | * | 11/1978 | Morman | A61F 13/26 604/227 |
| 4,198,978 A | * | 4/1980 | Nigro | A61F 13/26 604/14 |
| 4,447,222 A | * | 5/1984 | Sartinoranont | A61F 13/55185 604/15 |

(Continued)

FOREIGN PATENT DOCUMENTS

| | | |
|---|---|---|
| CN | 1600286 A | 3/2005 |
| JP | 3217617 B2 | 8/2001 |

(Continued)

OTHER PUBLICATIONS

Office Action dated Jun. 11, 2015, corresponding to Chinese patent application No. 201280038050.8.

(Continued)

*Primary Examiner* — Susan Su
(74) *Attorney, Agent, or Firm* — Hauptman Ham, LLP

(57) ABSTRACT

A tampon applicator includes an outer tube with an absorber stored inside, an inner tube inserted inside the outer tube and movable towards and into the outer tube to push the absorber to outside the outer tube, and an auxiliary grip member. The auxiliary grip member includes a cover unit covering an outer circumference surface of the grip unit, and a collar unit extending radially outwards from an outer circumference surface of the cover unit. A caved-in unit caving in from a terminal end of the cover unit towards a distal end side of the auxiliary grip member in a direction of insertion, in which the tampon applicator is configured to be inserted inside a vagina of the user, is formed in the terminal end of the cover unit.

6 Claims, 8 Drawing Sheets

(56) References Cited

U.S. PATENT DOCUMENTS

| | | | | |
|---|---|---|---|---|
| 5,395,309 | A * | 3/1995 | Tanaka | A61B 17/24 604/11 |
| 5,437,628 | A * | 8/1995 | Fox | A61F 13/26 604/1 |
| 5,447,499 | A * | 9/1995 | Allaire | A61F 13/26 602/42 |
| 5,709,652 | A * | 1/1998 | Hagerty | A61F 13/26 604/15 |
| 5,788,663 | A * | 8/1998 | Igaue | A61F 13/26 604/11 |
| 5,817,047 | A * | 10/1998 | Osborn, III | A61F 13/2051 604/14 |
| 6,322,531 | B1 * | 11/2001 | Cortese | A61F 13/26 604/15 |
| 6,572,577 | B1 * | 6/2003 | Binner | A61F 13/26 604/15 |
| 6,786,883 | B2 * | 9/2004 | Shippert | A61F 13/26 604/15 |
| 7,815,594 | B2 * | 10/2010 | Dougherty, Jr. | A61F 13/266 604/15 |
| 7,935,098 | B2 * | 5/2011 | Bartning | A61F 2/005 604/13 |
| 8,062,245 | B2 * | 11/2011 | Gann | A61F 13/26 604/15 |
| 8,075,512 | B2 * | 12/2011 | Sargent, Jr. | A61F 13/26 424/430 |
| 8,529,598 | B2 * | 9/2013 | Jenson | A61B 17/0057 604/15 |
| 8,961,449 | B2 * | 2/2015 | Jorgensen | A61F 13/2031 604/13 |
| 2002/0010413 | A1 | 1/2002 | Binner et al. | |
| 2007/0021708 | A1 * | 1/2007 | Bertulis | A61F 13/266 604/15 |
| 2008/0167599 | A1 | 7/2008 | Osborn et al. | |
| 2008/0195030 | A1 * | 8/2008 | Gann | A61F 13/26 604/15 |

FOREIGN PATENT DOCUMENTS

| | | |
|---|---|---|
| JP | 2003-180742 A | 7/2003 |
| JP | 2010-515520 A | 5/2010 |
| WO | 2008/084452 A1 | 7/2008 |
| WO | 2008/090667 A1 | 7/2008 |

OTHER PUBLICATIONS

International Search Report mailed Oct. 23, 2012, in International Application No. PCT/JP2012/068994, filed Jul. 26, 2012.
Extended European Search Report dated Mar. 25, 2015, corresponding to European patent application No. 12820148.0.
Office Action dated Oct. 28, 2014, corresponding to Chinese patent application No. 201280038050.8.
Office Action in CN Application No. 201280038050.8, mailed Nov. 24, 2015.
Office Action in TW Application No. 101124782, mailed Nov. 26, 2015.
Office Action in JP Patent Application No. 2011-167807, mailed Jan. 12, 2016.
Office Action in AU Patent Application No. 2012291212, mailed Feb. 16, 2016.
Office Action mailed Jul. 28, 2015, corresponding to Japanese patent application No. 2011-167807.

* cited by examiner

FIG. 3
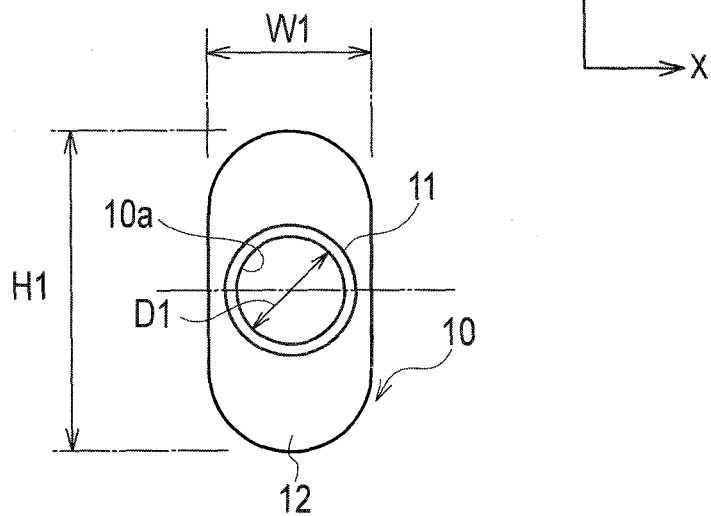
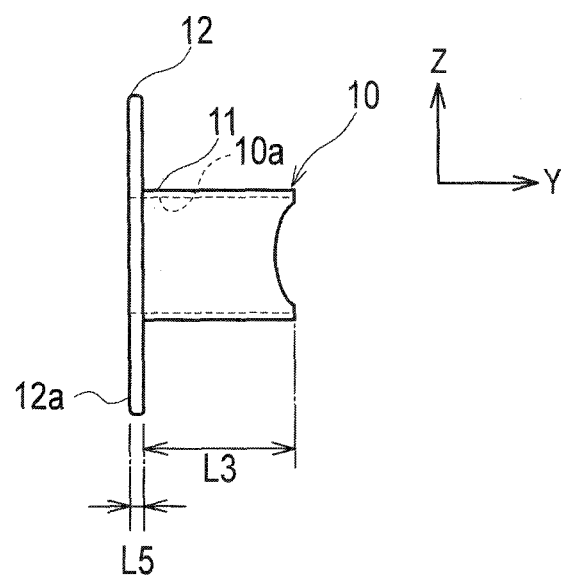

FIG. 5
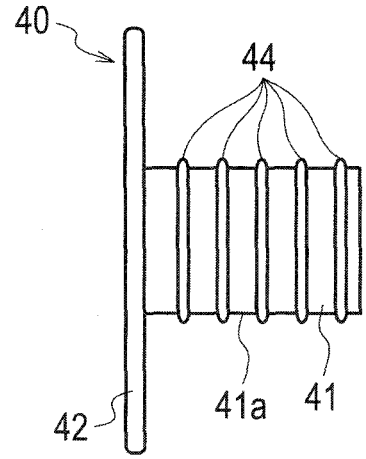
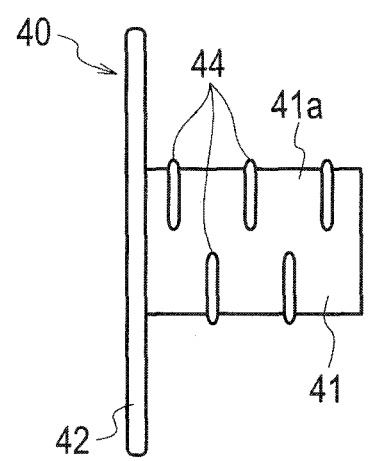
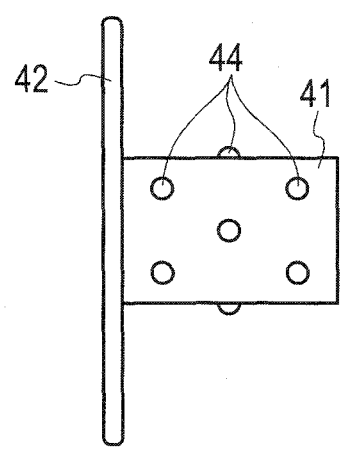

FIG. 7
(A)
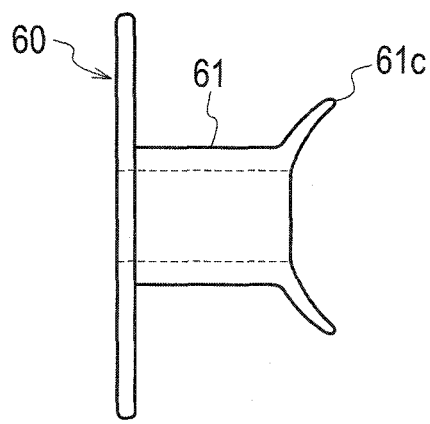
(B)
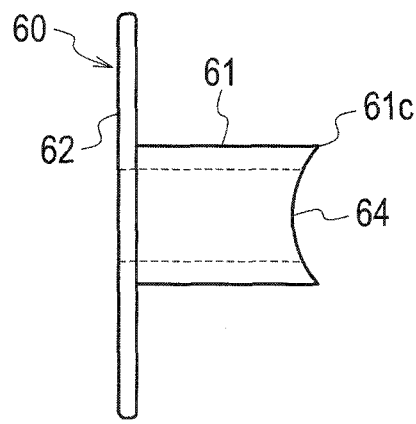
(C)
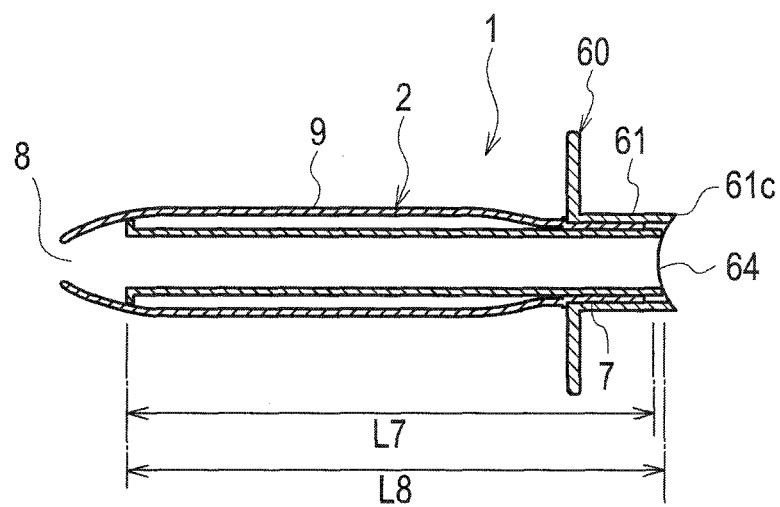

TAMPON APPLICATOR

RELATED APPLICATIONS

The present application is a National Phase of International Application No. PCT/JP2012/068994, filed Jul. 26, 2012, and claims priority from Japanese Application No. JP2011-167807, filed, Jul. 29, 2011.

TECHNICAL FIELD

The present invention relates to a tampon applicator.

BACKGROUND ART

Conventionally, a sanitary tampon with an applicator is provided. The tampon applicator includes an outer tube and an inner tube. An absorber having a withdrawal string is stored inside the outer tube. When using a sanitary tampon, the user inserts the outer tube inside the vagina while gripping the outer tube, and then presses the inner tube towards the outer tube. When the inner tube is pressed towards the outer tube, the absorber is pushed out from the outer tube and is arranged inside the vagina. However, when using a sanitary tampon, if the user pushes out the absorber when the outer tube has not been inserted up to an appropriate depth, the absorber is not arranged at an appropriate position inside the vagina.

Patent Literature 1 describes a tampon applicator made in view of this problem. The tampon applicator includes a collar unit extending out towards the circumference of the outer tube. When using the sanitary tampon, the user grips the outer tube via the collar unit, and inserts the outer tube inside the vagina. When the outer tube is inserted up to an appropriate depth, the collar unit comes in contact with the vaginal opening. Therefore, the user can insert the outer tube up to the appropriate depth. When the user pushes out the absorber with the outer tube inserted up to an appropriate depth, the absorber is arranged at an appropriate position inside the vagina.

PRIOR ART DOCUMENT

Patent Document

Patent Document 1: Japanese Patent Publication No. 3217617

SUMMARY OF INVENTION

However, the applicants noted the following potential problems as regard the aforementioned tampon applicator.

In the collar unit of the tampon applicator described in Patent Literature 1, a hole perforated in a thickness direction is formed, and the outer tube is inserted in the hole of the collar unit. As shown in FIG. 1 of Patent Literature 1, the collar unit has a relatively thin plate shape. Therefore, it may not be possible to secure a sufficient contact area between the collar unit and the outer circumference surface, and mounting the collar unit in a stable state onto the outer tube might not be possible. For example, if the position of the collar unit is misaligned at the time of inserting the outer tube in the body, it may not be possible to insert the outer tube while maintaining an appropriate angle of insertion, and arranging the absorber at an appropriate position inside the vagina might not be possible.

Thus, the present invention has been made in view of the above problems, and its purpose is to provide a tampon applicator that can easily dispose an absorber at an appropriate position inside the vagina.

To solve the above problems, a tampon applicator (tampon applicator 1) according to this invention, including: an outer tube (outer tube 2) with an absorber stored inside; an inner tube (inner tube 3) which is inserted inside the outer tube, which is movable towards into the outer tube to push the absorber (absorber 4) to the outside of the outer tube; and an auxiliary grip member (auxiliary grip member 10), wherein an aperture (aperture 8) by which the absorber is to be pushed out is formed at one end of the outer tube, and a grip unit (grip unit 7) to configured to be gripped by the user is formed at the other end of the outer tube, the auxiliary grip member includes a cover unit (cover unit 11) configured to cover an outer circumference surface of the grip unit of the outer tube, and a collar unit (collar unit 12) extending radially outwards from an outer circumferential surface (outer circumferential surface 11a) of the cover unit of the outer tube.

BRIEF DESCRIPTION OF DRAWINGS

FIG. 3 is a diagram showing an auxiliary grip member according to the first embodiment. (A) is a front view, and (B) is a side view.

FIGS. 5A-5C are diagrams showing an auxiliary grip member according to a second embodiment.

FIGS. 7A-7C are an auxiliary grip member according to a fourth embodiment.

DESCRIPTION OF EMBODIMENTS

First Embodiment

Figure 1:
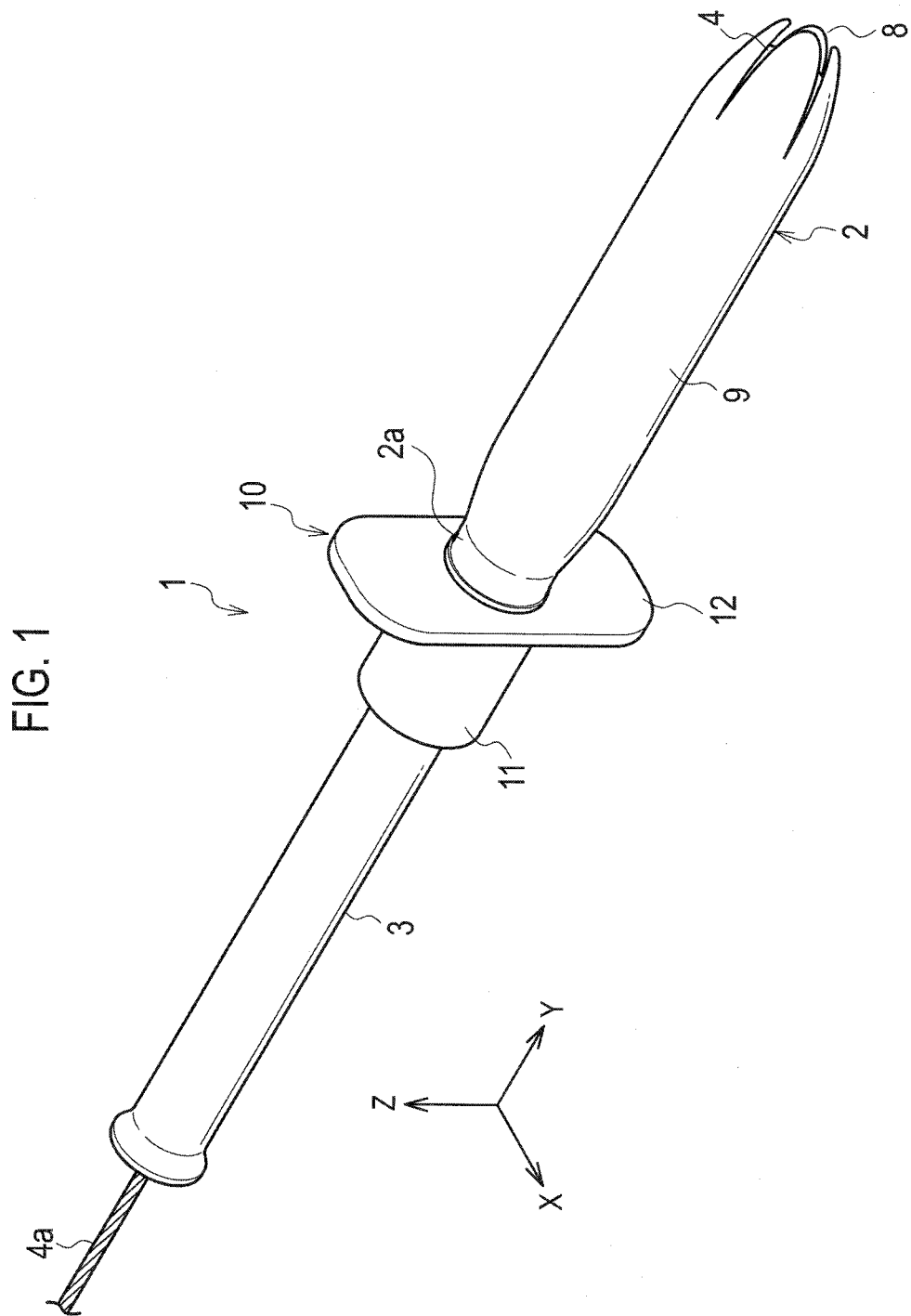
FIG. 1 is a perspective view of a tampon applicator according to a first embodiment of the present invention.
Figure 2:
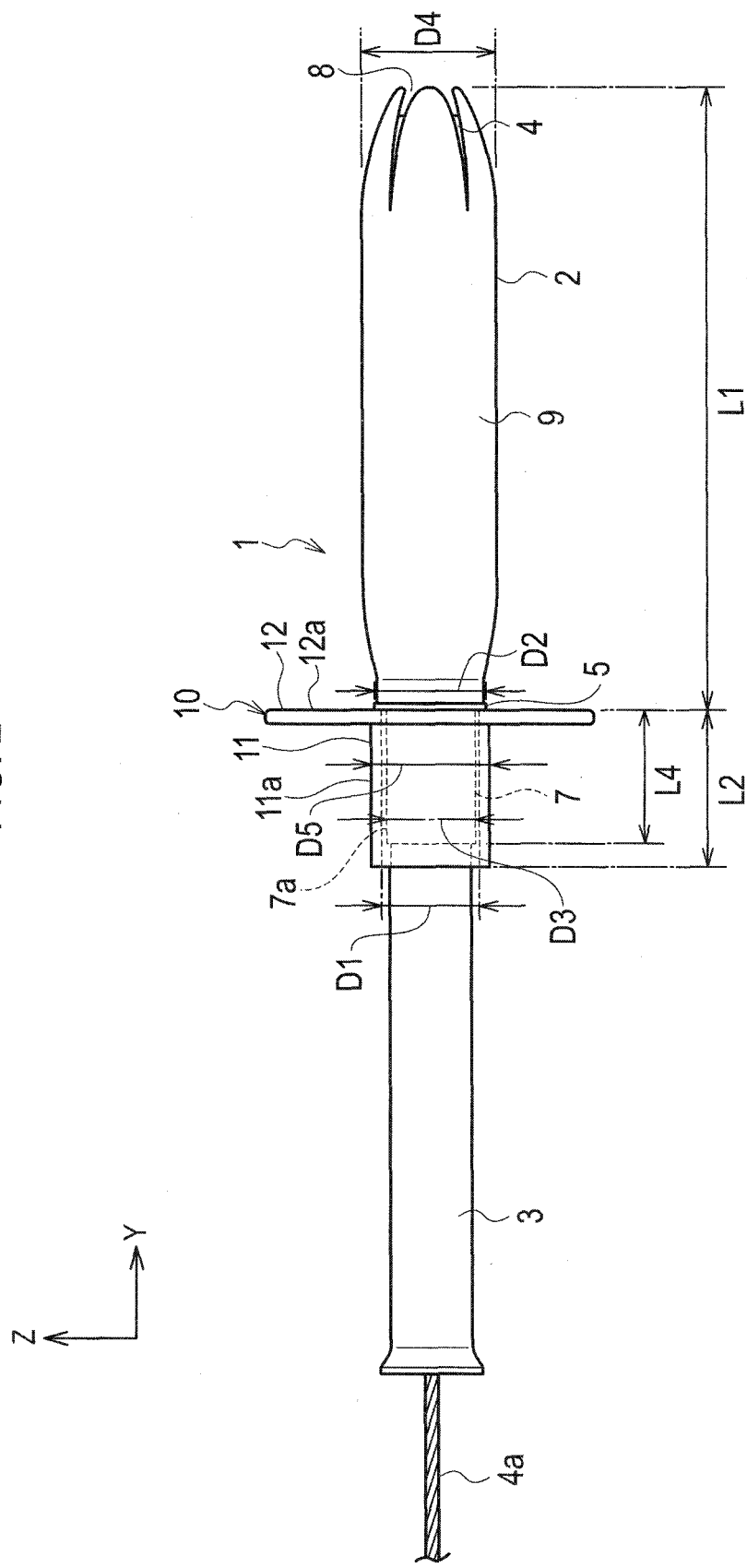
FIG. 2 is a plan view of the tampon applicator shown in FIG. 1.

The tampon applicator according to the first embodiment of the present invention is explained with reference to FIG. 1 and FIG. 2. FIG. 1 is a perspective view showing the entire tampon applicator according to the first embodiment, and FIG. 2 is a plan view of the tampon applicator shown in FIG. 1.

A tampon applicator 1 has an outer tube 2 and an inner tube 3. The outer tube 2 and the inner tube 3 are cylindrical in shape having a hollow portion therein. The cross-sectional shape of the outer tube 2 and the inner tube 3 is a precise circle. The outer tube 2 and the inner tube 3 are entirely formed by a polyolefin resin such as polyethylene and polypropylene, or by a cardboard whose surface is laminated with a polyolefin film.

In the present embodiment, the outer tube 2 and the inner tube 3 are formed by injection molding by mixing together polyethylene and polypropylene, 1% or more of a pigment, and 1% or more of a lubricant. Although the cross-sectional shape of the outer tube 2 and the inner tube 3 according to the present embodiment is a precise circle, the cross-sectional shape of the outer tube 2 and the inner tube 3 according to the present invention can also be of any shape, for example, an elliptical shape as long as it can be inserted easily inside the vagina.

Inside the outer tube 2 is contained an absorber 4 as a tampon. A withdrawal string 4a is connected to the absorber 4. The withdrawal string 4a is inserted inside the inner tube 3, extends from the end of the absorber 4, and the inserted end is extracted out from the inner tube 3. By pulling the withdrawal string 4a during use, the absorber 4 can be pulled out from inside the body.

An aperture 8 by which the absorber 4 is to be pushed out is formed at one end of the outer tube 2. In the aperture 8, a petal body 8a that is to be deformed radially outwards when the absorber 4 is pushed out is formed. The petal body 8a is formed by four split segments split up at every 90 degrees. The petal body 8a is always closed at an edge of the aperture 8, and when the absorber 4 is pushed out by the inner tube 3, it gets flared by the absorber 4 and opens up. Thus, the absorber 4 is pushed out from the outer tube 2, and can be inserted inside the body.

At the other end of the outer tube 2, a grip unit 7 that to be gripped by fingers during the movement operation of the outer tube 2 and the inner tube 3 is provided. The outer diameter D5 of the grip unit 7 is smaller than the outer diameter D4 of an outer tube main body 9 between the opening 8 and the grip unit 7. A tip portion of the inner tube 3 is inserted in the grip unit 7, and the tip surface of the inserted inner tube 3 faces the absorber 4. The end part of the outer tube main body 9 at the side of the grip unit 7 is narrowed to almost the same size in diameter as the grip unit 7, and has a protrusion 5.

The protrusion 5 is in contact with an auxiliary grip member 10 described later, and restrains the movement of the auxiliary grip member 10 such that the auxiliary grip member 10 does not move towards the aperture 8 side. The present embodiment is configured such that the auxiliary grip member 10 is in contact with the protrusion 5 of the outer tube 2 such that the movement of the auxiliary grip member 10 is restrained, however, it may be configured such that the auxiliary grip member 10 may be in contact with the outer circumference surface of the outer tube 2 such that the movement of the auxiliary grip member 10 is restrained.

The auxiliary grip member 10 arranged along the outer circumference of the grip unit 7 of the outer tube 2 is fitted in the grip unit 7. FIG. 3 is a diagram showing the auxiliary grip member 10. FIG. 3 (A) is a front view, and FIG. 3 (B) is a left-side view of FIG. 3 (A).

In the auxiliary grip member 10, a cover unit 11 covering an outer circumference surface 7a of the grip unit 7, and a collar unit 12 extending out towards the outer side of the radial direction (the X direction and Z direction shown in FIG. 1) of the outer tube 2 from an outer circumference surface 11a of the cover unit 11 are formed as one part.

A hole 10a in which the grip unit 7 is inserted is formed in the auxiliary grip member 10. The internal diameter D1 of the hole 10a is smaller than the outer diameter D2 of the protrusion 5. In the auxiliary grip member 10, a surface 12a of the collar unit 12 positioned at the distal end of the direction of insertion of the tampon applicator is in contact with the protrusion 5. The direction of insertion of the tampon applicator is arranged along the longitudinal direction of the tampon applicator (the Y direction shown in FIG. 2).

As a result of contact between the surface 12a of the collar unit 12 and the protrusion 5, the movement of the auxiliary grip member 10 towards the distal end side (aperture 8 side of the outer tube 2) of the direction of insertion is restrained.

The internal diameter D1 of the hole 10a is desired to be larger than the outer diameter of the grip unit 7 or the same as the outer diameter of the grip unit 7. The auxiliary grip member 10 can move in the circumferential direction and the axial direction of the grip unit 7.

In the applicator 1 for a tampon according to the present embodiment, the inner diameter D1 of the auxiliary grip member 10 is 11.6 mm, the outer diameter D4 of the outer tube main body 9 is 13.4 mm, the outer diameter D3 of the grip unit 7 is 10 mm, and the outer diameter D2 of the protrusion 5 is 13.4 mm. The outer diameter D5 of the cover unit is 13.2 mm.

The length L1 in the longitudinal direction Y from the end of the outer tube 2 at the side of the aperture up to the auxiliary grip member 10 is 53.05 mm, and the length L2 in the longitudinal direction Y of the auxiliary grip member 10 is 16 mm.

The cover unit 11 is cylindrical. The shape of the collar unit 12 in the front view of the auxiliary grip member shown in FIG. 3 (A) is rectangular with curved four corners. The four corners of the collar unit 12 are circular arcs with a radius R=7.5 mm. The width W1 of the collar unit 12 shown in FIG. 3 (A) is 16 mm, and the height H1 of the collar unit 12 is 32 mm. The ratio of the width of the collar unit 12 with respect to the height thereof is 0.41. The height H1 of the collar unit is desired to be longer than the outer diameter D5 of the cover unit 11 at least.

The length L4 in the longitudinal direction Y of the grip unit 7 is equal to or smaller than the length L3 in the longitudinal direction of the cover unit 11. The length L3 of the cover unit in the present embodiment is 15.2 mm and the length L4 of the grip unit is 13.5 mm. The length of the cover unit 11 is desired to be such that the user can hold the cover unit with her fingers, and is specifically desired to be in the range of 5 mm to 20 mm approx. Furthermore, the length L5 (thickness of the collar unit 12) in the longitudinal direction Y of the collar unit 12 is 0.8 mm.

By configuring the length L3 of the cover unit 11 longer than the length L4 of the grip unit 7, the area that the user can hold, when the auxiliary grip member 10 is fitted, can be increased. Therefore, when inserting the tampon applicator inside the body, the user can hold the grip unit firmly, and can insert the tampon applicator in a stable state.

The auxiliary grip member 10 is configured from a polyolefin resin, an elastomer, paper, or any other material. The auxiliary grip member 10 according to the present embodiment is configured from a polyethylene and polypropylene resin.

Figure 4:
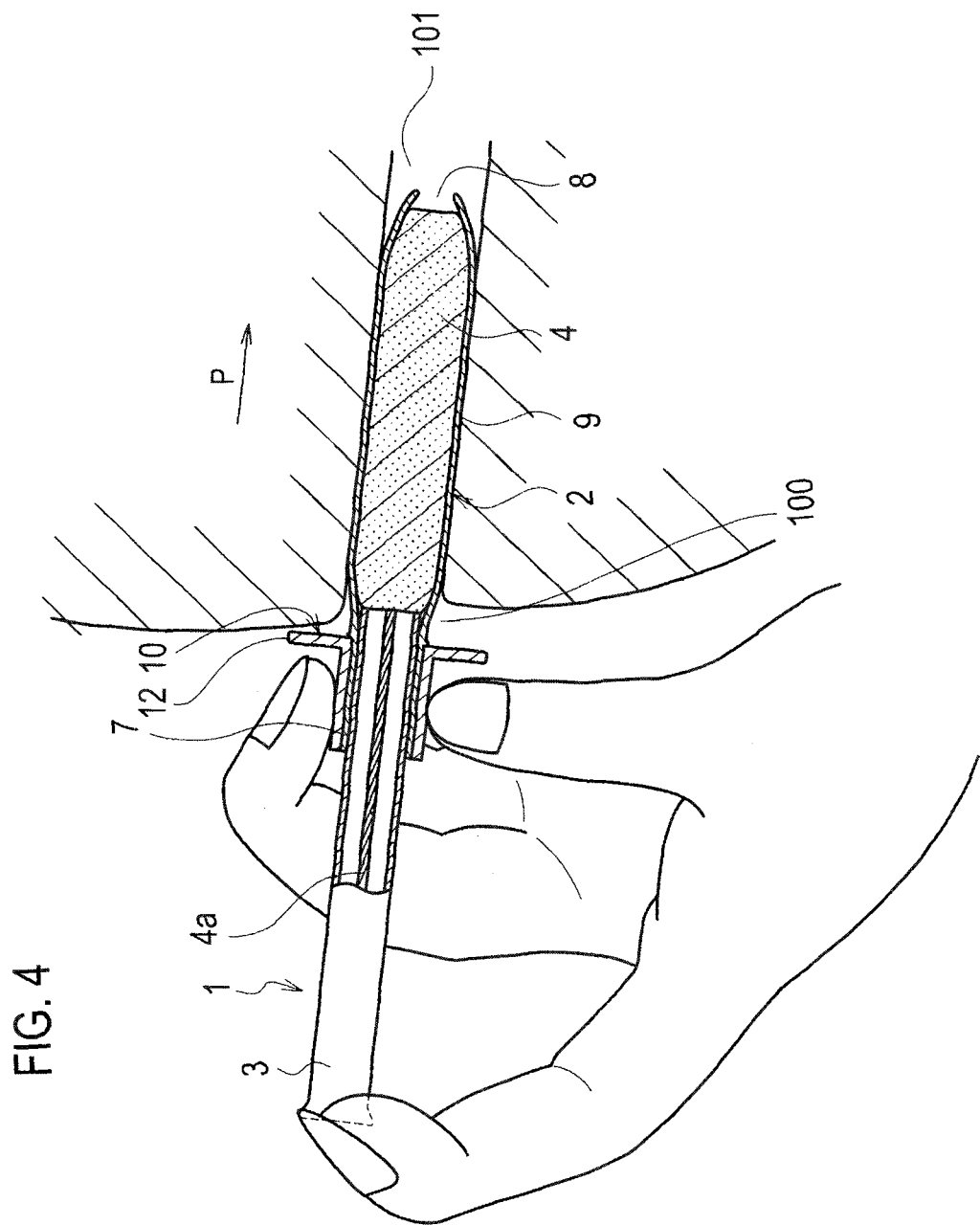
FIG. 4 is a schematic front view showing a form of usage of the tampon applicator shown in FIG. 1.

Next, a form of usage of a tampon applicator thus configured is explained. FIG. 4 is a schematic cross-sectional view showing a form of usage of a tampon applicator. With the distal end of the outer tube 2 in contact with a vaginal opening 100, the user presses the auxiliary grip member 10 in the direction of insertion of the outer tube inside the vagina 101. Because the surface 12a of the collar unit 12 of the auxiliary grip member 10 is in contact with the protrusion 5 of the outer tube 2, the movement of the auxiliary grip member 10 towards the opening side of the outer tube 2 is restrained. Thus, when the user presses the auxiliary grip member 10 towards the inside of the vagina 101, the outer tube 2 is inserted inside the vagina.

Because the collar unit 12 is arranged at the distal end side of the auxiliary grip member 10 in the direction of insertion (P shown in FIG. 4) of the applicator 1 for a tampon inside the vagina 101, the surface 12a of the collar unit 12 is arranged in the proximity of the vaginal opening, with the outer tube 2 inserted up to an appropriate position. Even when an attempt is made to further insert the outer tube 2 in such a state, the collar unit 12 comes in contact with the body of the user. That is, the collar unit 12 exhibits the function of a stopper, and the user can understand that she has been able to insert the outer tube 2 up to the appropriate position.

Furthermore, when the outer tube 2 has been inserted up to the appropriate position, the collar unit 12 is arranged between the vaginal opening 100 and the fingers. At this time, because the width W1 of the collar unit 12 is longer than the outer diameter D5 of the cover unit 11, the collar unit 12 is arranged between the fingers holding the auxiliary grip member 10 and the vaginal opening 100, and soiling of the user's fingers due to the bodily fluid, such as menstrual blood, can be prevented.

Next, when the user inserts the outer tube 2 up to a predetermined position inside the vagina 101, and then presses the inner tube 3 towards the aperture 8 side of the outer tube 2, the absorber 4 is pushed out from the aperture 8 of the outer tube 2, and the absorber 4 is arranged at an appropriate position inside the vagina. By thus including the collar unit 12, the absorber 4 can be arranged easily at the appropriate position without the user's fingers touching the area near the vaginal opening. By arranging the absorber 4 at the appropriate position, the feeling of discomfort of the user at the time of using the tampon applicator is reduced, and the use of tampon can be thought of as being comfortable.

Because the auxiliary grip member 10 includes the cover unit 11 that covers the outer circumference surface 7a of the grip unit 7, and the cover unit 11 and the collar unit 12 are formed as one part, it becomes easy to maintain the angle of the auxiliary grip member 10 with respect to the grip unit 7 of the outer tube 2 at a constant value. Therefore, the outer tube 2 is inserted inside the body while maintaining the collar unit 12 and the grip unit 7 at an appropriate angle, and the absorber 4 can be arranged at an appropriate position inside the vagina.

Furthermore, because the auxiliary grip member 10 can be rotated with respect to the grip unit 7, when inserting the outer tube 2 inside the body while holding the auxiliary grip member 10, the outer tube 2 can be inserted inside the body while maintaining the appropriate angle, by rotating the auxiliary grip member 10 with respect to the outer tube 2.

Specifically, the angle and position of the hand holding the applicator 1 for a tampon changes in the state when the aperture, which is the distal end of the outer tube 2, is in contact with the vaginal opening, and in the state when the outer tube 2 is inserted inside the vagina and the collar unit 12 is in contact with the vaginal opening 100. At this time, by rotating the auxiliary grip member 10 with respect to the outer tube 2, the relative angle between the collar unit 12 and the outer tube 2 can be changed in accordance with the change in the position and angle of the hand with respect to the applicator 1 for a tampon. Therefore, even when the angle and position of the hand holding the applicator 1 for a tampon changes, the user can smoothly insert the tampon applicator by exerting an appropriate force to the tampon applicator.

The auxiliary grip member 10 of the present embodiment is formed by injection-molding of a thermoplastic resin using a mold. When injection-molding, the auxiliary grip member 10 may be molded together with the outer tube 2, or may be molded separately and then fitted through a single-unit forming step during the manufacturing process. Furthermore, the auxiliary grip member 10 may be configured in a detachable manner with respect to the outer tube 2, and may also be configured to be fitted by the user before use.

The rigidity of the cover unit 11 of the auxiliary grip member 10 is desired to be more than the rigidity of the grip unit 7 of the outer tube 2. For example, if the rigidity of the cover unit 11 is low, the cover unit 11 gets deformed when the user holds the cover unit, and is pressed against the inner side of the outer tube 2 thus reducing the gap between the outer tube 2 and the inner tube 3, and the inner tube 3 cannot be pushed out smoothly. However, because the rigidity of the cover unit 11 of the auxiliary grip member 10 is higher than the rigidity of the grip unit 7 of the outer tube 2, the deformation of the grip unit 7 of the outer tube 2 can be prevented, and it becomes easy to push out the inner tube 3 smoothly.

Examples of configurations in which the rigidity of the cover unit 11 of the auxiliary grip member 10 is higher than the rigidity of the grip unit of the outer tube include, for example, a configuration in which the material of the cover unit of the auxiliary grip member 10 is harder than the material of the grip unit, and a configuration in which the thickness of the cover unit 11 of the auxiliary grip member 10 is more than the thickness of the grip unit.

Second Embodiment

Next, an auxiliary grip member 40 according to a second embodiment is explained based on FIG. 5. In the explanation of the below embodiment, only the configuration that is different from the first embodiment has been explained, and the same symbols have been used for the configuration that is the same as the first embodiment while omitting the explanation.

The auxiliary grip member 40 according to the second embodiment includes a cover unit 41 and a collar unit 42. Protrusions 44 protruding out towards the outside of the radial direction from an outer circumference surface of the cover unit 41 are formed on the outer circumference surface 41a of the cover unit 41.

Because the protrusions 44 are formed on the outer circumference surface of the cover unit, the fingers of the user touch the protrusions 44 when the user holds the cover unit, which makes it difficult for the fingers to slide. Therefore, the outer tube is inserted inside the body while maintaining the collar unit and the grip unit at an appropriate angle, and the absorber can be arranged at an appropriate position inside the vagina.

As regards the shape of the protrusions 44, the protrusions may be formed in a continuous ring shape in the circumferential direction along the circumferential direction of the cylindrical cover unit, as shown in FIG. 5 (A), or may be formed in a discontinuous circular arc in the circumferential direction along the circumferential direction of the cylindrical cover unit, as shown in FIG. 5 (B), or may be formed as dots arranged intermittently, as shown in FIG. 5 (C).

The protrusions 44 may be molded by injection-molding, laser molding, heat molding, and other methods. The protrusions 44 can have the shape of a straight line, a symmetrical shape, a dot shape, rhomboid, or a heart shape. The height of the protrusions with respect to the outer circumference surface of the cover unit is desired to be 1 mm or more, and as shown in FIG. 5 (A), the protrusions are desired to be formed over the entire circumference of the cover unit 41.

Third Embodiment

Figure 6:
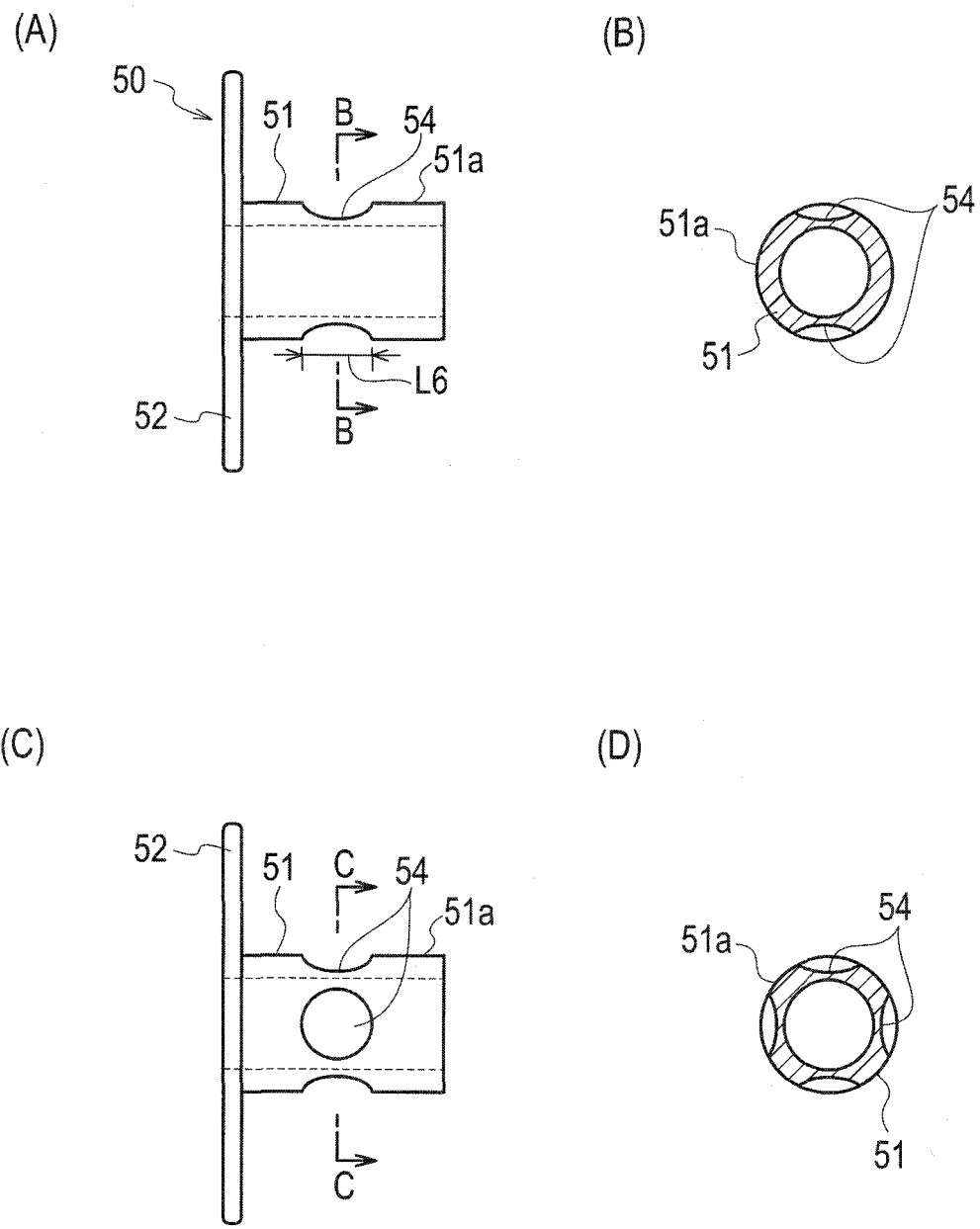
FIGS. 6A-6D are diagrams showing an auxiliary grip member according to a third embodiment.

Next, an auxiliary grip member 50 according to a third embodiment is explained based on FIG. 6. FIG. 6 (A) and FIG. 6 (C) are front views of the auxiliary grip members 50 according to the third embodiment, FIG. 6 (B) is a cross-sectional view of FIG. 6 (A) along the arrow B-B, and FIG. 6 (D) is a cross-sectional view of FIG. 6 (C) along the arrow C-C.

The auxiliary grip member 50 according to the third embodiment includes a cover unit 51 and a collar unit 52. Concavities 54 recessed towards the inside of the radial direction from the outer circumference surface of the cover unit are formed in an outer circumference surface 51a of the cover unit 51.

Because the concavities 54 are formed on the outer circumference surface of the cover unit, the user can arrange her fingers along the recessed units when holding the cover unit, which makes it difficult for the fingers to slip. The length L6 of the recessed units 54 in the longitudinal direction can be set as the length in which the fingers can be arranged, and specifically, a length of 3 mm to 5 mm is desired.

As shown in FIG. 6 (A) and FIG. 6 (B), two concavities 54 may be formed along the outer circumference surface of the cover unit, and as shown in FIG. 6 (C) and FIG. 6 (D), four concavities 54 may be formed along the outer circumference surface of the cover unit.

Fourth Embodiment

Next, an auxiliary grip member 60 according to a fourth embodiment is explained based on FIG. 7. FIG. 7 (A) and FIG. 7 (B) are side views of the auxiliary grip member 60 according to the fourth embodiment, and FIG. 7 (C) is a diagram schematically illustrating a form of usage of the auxiliary grip member 60 shown in FIG. 7 (B).

The auxiliary grip member 60 according to the fourth embodiment includes a cover unit 61 and a collar unit 62. A caved-in unit 64 caving in from a terminal end 61c towards the distal end side in the direction of insertion is formed in the terminal end 61c of the cover unit 61 in the direction of insertion of the tampon applicator.

By forming at least one or more caved-in units 64 in the terminal end of the cover unit, the inner tube can be pushed in towards the inner side from the position of the terminal end of the cover unit.

Furthermore, FIG. 7 (C) shows the state when the distal end of the inner tube 3 in the direction of insertion is in contact with the inner circumference of the outer tube 2. In such a state, the length L7 from the distal end of the inner tube 3 up to the caved-in unit 64 of the auxiliary grip member 60 is shorter than the length L8 in the longitudinal direction of the inner tube.

Because the length L7 from the distal end of the inner tube 3 up to the caved-in unit 64 of the auxiliary grip member 60 is shorter than the length L8 in the longitudinal direction of the inner tube, even when the length in the longitudinal direction of the cover unit is configured to be long in order to secure a wide area for the cover unit, the entire inner tube can be pushed inside the outer tube, and the absorber can be pushed out appropriately by the inner tube.

Fifth Embodiment

Figure 8:
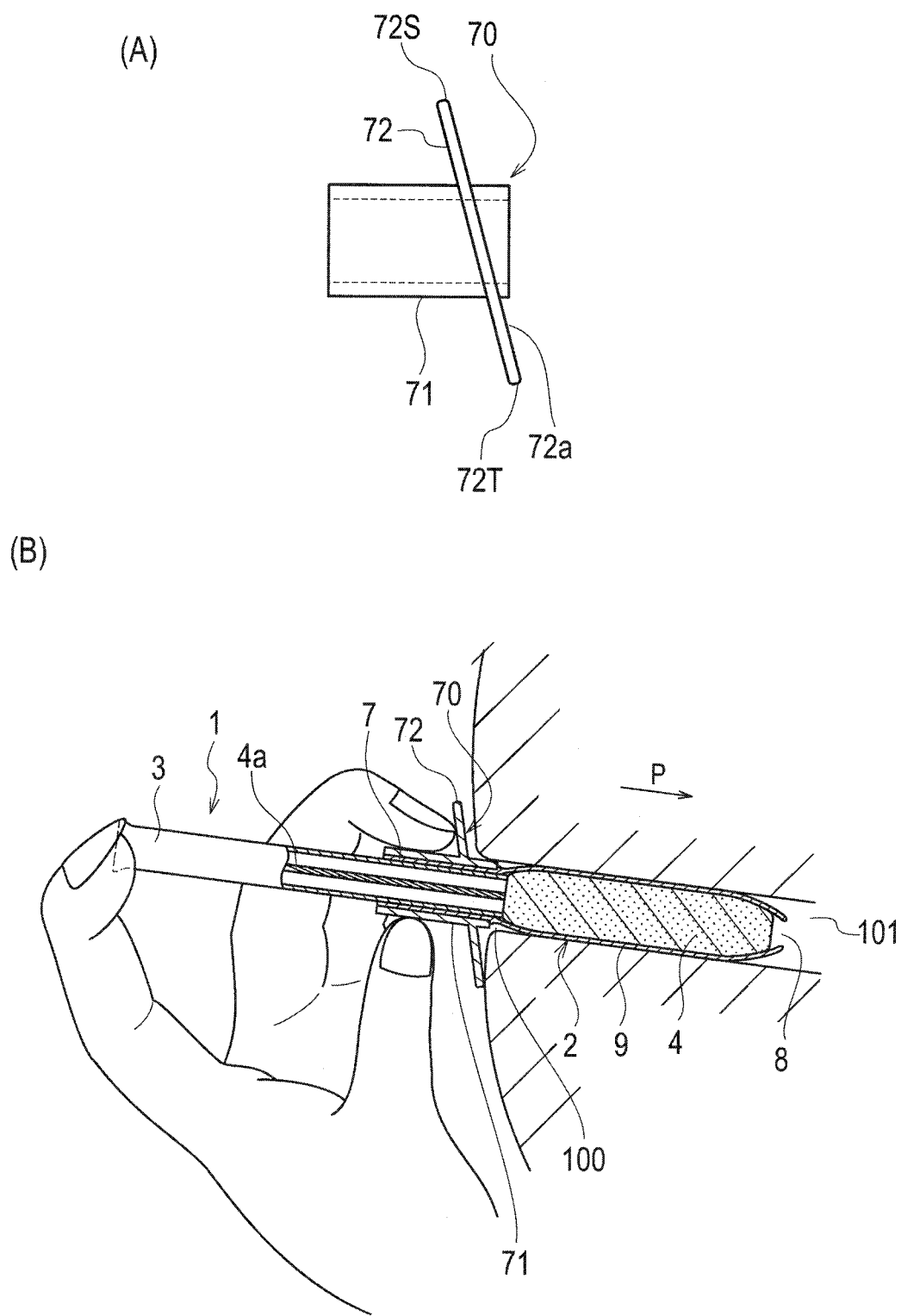
FIGS. 8A-8B are diagrams showing an auxiliary grip member according to a fifth embodiment.

Next, an auxiliary grip member 70 according to a fifth embodiment is explained based on FIG. 8. FIG. 8 (A) is a side view of the auxiliary grip member 70 according to the fifth embodiment, and FIG. 8 (B) is a diagram schematically illustrating a form of usage of the auxiliary grip member 70.

The auxiliary grip member 70 according to the fifth embodiment includes a cover unit 71 and a collar unit 72. The surface 12a of the collar unit 12 of the auxiliary grip member 10 according to the first embodiment is arranged almost perpendicular to the outer circumference surface of the cover unit 11. By contrast, the surface 72a of the collar unit 72 of the fifth embodiment is arranged at an inclination and not perpendicular to the outer circumference surface of the cover unit 71.

Furthermore, the collar unit 12 of the first embodiment is arranged at the distal end in the direction of insertion of the cover unit 11, however, the collar unit 72 of the fifth embodiment is arranged posteriorly in the direction of insertion from the distal end of the cover unit 71. A portion 72S of the outer peripheral edge of the collar unit 72, which is the outer side in the radial direction of the outer tube 2, is arranged posterior to the distal end of the cover unit 71, however, the other portion 72T of the outer peripheral edge of the collar unit 72 is arranged anterior to the distal end of the cover unit 71.

FIG. 8 (B) shows a form of usage of the applicator 1 for a tampon when the auxiliary grip member 70 is fitted in the outer tube 2. When the user is in a standing position, the vaginal opening of the user is generally arranged almost perpendicular to the axial direction of the vagina. Therefore, as in the first embodiment, when the axial direction of the outer tube is arranged vertically by using the tampon applicator in which the collar unit 12 is arranged almost perpendicular to the outer circumference surface of the outer tube 2, the surface of the collar unit 12 can be arranged opposite the vaginal opening.

However, when the user is sitting, the vaginal opening of the user is generally arranged at an inclination to the axial direction of the vagina. At this time, as in the first embodiment, if a tampon applicator in which the collar unit is arranged almost perpendicular to the outer circumference surface of the outer tube is used, the surface of the collar unit is not arranged opposite the vaginal opening, but a gap may be generated between the surface of the collar unit and the vaginal opening, when the outer tube 2 is inserted up to an appropriate position. However, by using the tampon applicator according to the fifth embodiment, when the tampon applicator is inserted up to the appropriate position, then as shown in FIG. 8 (B), the entire surface of the collar unit 72 can be brought in contact with the vaginal opening, and the user can understand that she has been able to insert the tampon applicator up to the appropriate position.

Thus, the present invention naturally includes various embodiments, not described herein. Therefore, the technical range of the present invention is to be defined only by the inventive specific matter according to the adequate claims from the above description.

For example, the collar unit of the auxiliary grip member may have an outer shape other than a rectangular shape in the plan view, and may have a polygon shape such as a rectangular shape or a triangular shape, or a heart shape, a star shape, an apple shape, an elliptical shape, or a teardrop shape, or the shape of the skull of animals, or else the shape of insects such as a butterfly. For example, by shaping the outer shape of the collar unit into a heart shape and the shape of the skull of animals, a medical device like a tampon can be beautified by the collar unit. Thus, the depressing feeling of the user associated with menstruation can be eased, and the willingness for subsequent use can be increased.

Furthermore, by adding a color to the collar unit, the decorative effect can be improved further. The color added to the collar unit is not particularly limited, for example, red and pink color can be added to a heart-shaped collar unit, and brown color can be added to a collar unit shaped like the head of a bear. Finally, by coloring the collar unit, the collar unit can be distinguished, and the handling becomes easy particularly in dimly lit places, such as toilets.

Furthermore, the outer circumferential shape of the collar unit is desired to be curved. The curved shape indicates that the configuration may be such that sharp angular portions are not included, and a linear shape may be included partially. By shaping the outer circumference surface of the collar unit in a curved shape, the feeling of holding the collar unit experienced by the user can be mellowed down.

Furthermore, the collar unit of the auxiliary grip member need not necessarily be arranged at the distal end of the cover unit in the direction of insertion, and may be arranged posterior to the distal end of the cover unit. When the configuration is such that the collar unit is arranged posterior to the distal end of the cover unit, the distal end of the cover unit is configured to come in contact with the outer circumference surface of the outer tube and the protrusions, and the movement of the auxiliary grip member towards the distal end is restrained.

The entire contents of Japanese Patent Application No. 2011-167807 (filed on Jul. 29, 2011) are incorporated in the present specification by reference.

INDUSTRIAL APPLICABILITY

The auxiliary grip member according to the present invention includes a cover unit configured to cover the grip unit of the outer tube, and a collar unit, and the tampon applicator, which the user use by gripping the cover unit and the collar unit, can be provided.

Because the collar unit extends out from the outer circumference surface of the cover unit covering the outer circumference surface of the outer tube towards the outer side of a radial direction, the position corresponding to the grip unit of the outer tube is stabilized as compared to a case when only the collar unit is fitted in the grip unit. Therefore, the tampon applicator, which the misalignment of the collar unit and the grip unit with the outer tube can be prevented, the outer tube is inserted inside the body while maintaining the collar unit and the grip unit at an appropriate angle, and the absorber can be arranged at an appropriate position inside the vagina, can be provided.

REFERENCE SIGNS LIST

1: tampon applicator
2: outer tube
2a: circumference surface
3: inner tube
4: absorber
4a: withdrawal string
5: protrusion
7: grip unit
7a: circumference surface
8: aperture
8a: petal body
9: outer tube main body
10, 20, 30, 40, 50, 60: auxiliary grip member
10a, 20a, 30a: hole
11,21,31,41,51,61: cover unit
11a,21a,31a,41a,51a,61a: outer circumference surface
12,22,32,42,52,62: collar unit
23,33: first concavo-convex unit
24,34: second concavo-convex unit
54: concavity
64: caved-in unit
100: vaginal opening
101: inside the vagina

The invention claimed is:

1. A tampon applicator, comprising:
   an outer tube with an absorber stored inside;
   an inner tube inserted inside the outer tube and movable towards and into the outer tube to push the absorber to outside the outer tube; and
   an auxiliary grip member,
wherein
   an aperture through which the absorber is configured to be pushed out is formed at one end of the outer tube, and a grip unit configured to be gripped by a user is formed at the other end of the outer tube,
   the auxiliary grip member includes
       a cover unit covering an outer circumference surface of the grip unit of the outer tube, and
       a collar unit extending radially outwards from an outer circumferential surface of the cover unit,
   a caved-in unit caving in from a terminal end of the cover unit towards a distal end side of the auxiliary grip member in a direction of insertion, in which the tampon applicator is configured to be inserted inside a vagina of the user, is formed in the terminal end of the cover unit, and
   in a state when a distal end of the inner tube in the direction of insertion is in contact with an inner circumference of the outer tube, a length from the distal end of the inner tube up to the caved-in unit of the auxiliary grip member is shorter than a length of the inner tube in a longitudinal direction of the tampon applicator.

2. The tampon applicator according to claim 1, wherein the collar unit is arranged at the distal end side of the auxiliary grip member in the direction of insertion.

3. The tampon applicator according to claim 1, wherein a length of the cover unit in the longitudinal direction is greater than a length of the grip unit in the longitudinal direction.

4. The tampon applicator according to claim 1, wherein the cover unit includes a protrusion protruding radially and outwardly from the outer circumference surface of the cover unit.

5. The tampon applicator according to claim 1, wherein the cover unit includes a concavity recessed radially and inwardly from the outer circumference surface of the cover unit.

6. The tampon applicator according to claim 1, wherein a rigidity of the cover unit of the auxiliary grip member is higher than a rigidity of the grip unit of the outer tube.

* * * * *